(12) United States Patent
Shelton, IV et al.

(10) Patent No.: US 8,460,337 B2
(45) Date of Patent: Jun. 11, 2013

(54) SELECTABLE HANDLE BIASING

(75) Inventors: Frederick E. Shelton, IV, Hillsboro, OH (US); Stuart K. Morgan, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 211 days.

(21) Appl. No.: 12/796,908

(22) Filed: Jun. 9, 2010

(65) Prior Publication Data

US 2011/0307005 A1   Dec. 15, 2011

(51) Int. Cl.
*A61B 17/00* (2006.01)
(52) U.S. Cl.
USPC ............................ 606/205; 606/167; 606/170
(58) Field of Classification Search
USPC ................. 606/205, 206, 207, 208, 209, 210, 606/211, 1, 171, 142, 143, 139, 108, 167–170
See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,306,545 A | 12/1981 | Ivan et al. |
| 4,373,532 A | 2/1983 | Hill et al. |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |
| 4,669,473 A | 6/1987 | Richards et al. |
| 4,821,719 A | 4/1989 | Fogarty |
| 4,831,070 A | 5/1989 | McInally et al. |

(Continued)

FOREIGN PATENT DOCUMENTS

| | | |
|---|---|---|
| EP | 0568383 | 11/1993 |
| EP | 621009 | 10/1994 |

(Continued)

OTHER PUBLICATIONS

"1 Lap Disc Hand Access Device—Ref. Ld111," by Ethicon Endo-Surgery, Inc. (date unknown but no later than May 15, 2007, date of citation in U.S. Appl. No. 11/398,985; 1 page).

(Continued)

*Primary Examiner* — Gary Jackson
*Assistant Examiner* — Katrina Stransky
(74) *Attorney, Agent, or Firm* — Nutter McClennen & Fish LLP

(57) ABSTRACT

Devices and related methods are disclosed that generally relate to surgical devices provided for use in various surgical procedures. In some embodiments, the surgical devices can include a handle housing and an elongate shaft having opposed jaws disposed at a distal end thereof. The handle housing can have a handle portion and a trigger configured to pivot relative to the handle portion to open and close the opposed jaws. A biasing switch can generally be disposed in and/or on the handle housing and can be selectively movable between a first configuration in which the opposed jaws are biased to an open position, and a second configuration in which the opposed jaws are biased to a closed position.

21 Claims, 4 Drawing Sheets

U.S. PATENT DOCUMENTS

| | | | |
|---|---|---|---|
| 4,880,015 A | 11/1989 | Nierman | |
| 5,027,800 A | 7/1991 | Rowland | |
| 5,141,498 A | 8/1992 | Christian | |
| 5,183,471 A | 2/1993 | Wilk | |
| 5,197,955 A | 3/1993 | Stephens et al. | |
| 5,201,742 A | 4/1993 | Hasson | |
| 5,207,213 A | 5/1993 | Auhll et al. | |
| 5,209,737 A | 5/1993 | Ritchart et al. | |
| 5,209,741 A | 5/1993 | Spaeth | |
| 5,209,747 A | 5/1993 | Knoepfler | |
| 5,269,772 A | 12/1993 | Wilk | |
| 5,275,614 A | 1/1994 | Haber et al. | |
| 5,308,336 A | 5/1994 | Hart et al. | |
| 5,312,023 A | 5/1994 | Green et al. | |
| 5,330,437 A | 7/1994 | Durman | |
| 5,330,502 A | 7/1994 | Hassler et al. | |
| 5,342,396 A | 8/1994 | Cook | |
| 5,345,927 A | 9/1994 | Bonutti | |
| 5,350,391 A | 9/1994 | Iacovelli | |
| 5,360,428 A | 11/1994 | Hutchinson, Jr. | |
| 5,362,294 A | 11/1994 | Seitzinger | |
| 5,366,478 A | 11/1994 | Brinkerhoff et al. | |
| 5,368,597 A | 11/1994 | Pagedas | |
| 5,374,277 A | 12/1994 | Hassler | |
| 5,383,888 A | 1/1995 | Zvenyatsky et al. | |
| 5,385,553 A | 1/1995 | Hart et al. | |
| 5,385,560 A | 1/1995 | Wulf | |
| 5,391,154 A | 2/1995 | Young | |
| 5,398,617 A | 3/1995 | Deandrea | |
| 5,403,342 A | 4/1995 | Tovey et al. | |
| 5,417,203 A | 5/1995 | Tovey et al. | |
| 5,443,452 A | 8/1995 | Hart et al. | |
| 5,443,484 A | 8/1995 | Kirsch et al. | |
| 5,445,648 A | 8/1995 | Cook | |
| 5,456,684 A | 10/1995 | Schmidt et al. | |
| 5,470,328 A * | 11/1995 | Furnish et al. | 606/1 |
| 5,480,410 A | 1/1996 | Cuschieri et al. | |
| 5,489,256 A | 2/1996 | Adair | |
| 5,489,290 A | 2/1996 | Furnish | |
| 5,501,653 A | 3/1996 | Chin | |
| 5,514,157 A | 5/1996 | Nicholas et al. | |
| 5,520,609 A | 5/1996 | Moll et al. | |
| 5,520,678 A | 5/1996 | Heckele et al. | |
| 5,545,123 A | 8/1996 | Ortiz et al. | |
| 5,545,179 A | 8/1996 | Williamson, IV | |
| 5,547,458 A | 8/1996 | Ortiz et al. | |
| 5,549,637 A | 8/1996 | Crainich | |
| 5,569,205 A | 10/1996 | Hart et al. | |
| 5,569,254 A | 10/1996 | Carlson et al. | |
| 5,571,090 A | 11/1996 | Sherts | |
| 5,582,577 A | 12/1996 | Lund et al. | |
| 5,582,617 A | 12/1996 | Klieman et al. | |
| 5,584,850 A | 12/1996 | Hart et al. | |
| 5,586,977 A | 12/1996 | Dorsey, III | |
| 5,591,182 A | 1/1997 | Johnson | |
| 5,595,193 A | 1/1997 | Walus et al. | |
| 5,607,450 A | 3/1997 | Zvenyatsky et al. | |
| 5,609,601 A | 3/1997 | Kolesa et al. | |
| 5,618,294 A | 4/1997 | Aust et al. | |
| 5,624,381 A | 4/1997 | Kieturakis | |
| 5,626,608 A | 5/1997 | Cuny et al. | |
| 5,630,831 A | 5/1997 | Lahr | |
| 5,634,882 A | 6/1997 | Gagner | |
| 5,634,883 A | 6/1997 | Chin et al. | |
| 5,634,911 A | 6/1997 | Hermann et al. | |
| 5,634,937 A | 6/1997 | Mollenauer et al. | |
| 5,636,645 A | 6/1997 | Ou | |
| 5,640,977 A | 6/1997 | Leahy et al. | |
| 5,643,283 A | 7/1997 | Younker | |
| 5,643,301 A | 7/1997 | Mollenauer | |
| 5,647,372 A | 7/1997 | Tovey et al. | |
| 5,653,705 A | 8/1997 | de la Torre et al. | |
| 5,665,093 A | 9/1997 | Atkins et al. | |
| 5,667,527 A | 9/1997 | Cook | |
| 5,672,168 A | 9/1997 | de la Torre et al. | |
| 5,676,146 A | 10/1997 | Scarborough | |
| 5,676,657 A | 10/1997 | Yoon | |
| 5,681,324 A | 10/1997 | Kammerer et al. | |
| 5,695,448 A | 12/1997 | Kimura et al. | |
| 5,700,275 A | 12/1997 | Bell et al. | |
| 5,704,534 A | 1/1998 | Huitema et al. | |
| 5,713,919 A | 2/1998 | Lahr | |
| 5,716,327 A | 2/1998 | Warner et al. | |
| 5,716,407 A | 2/1998 | Knapp et al. | |
| 5,728,121 A | 3/1998 | Bimbo et al. | |
| 5,735,289 A | 4/1998 | Pfeffer et al. | |
| 5,743,456 A | 4/1998 | Jones et al. | |
| 5,743,851 A | 4/1998 | Moll et al. | |
| 5,766,205 A | 6/1998 | Zvenyatsky et al. | |
| 5,772,654 A | 6/1998 | Leyva | |
| 5,782,812 A | 7/1998 | Hart et al. | |
| 5,782,859 A | 7/1998 | Nicholas et al. | |
| 5,792,165 A | 8/1998 | Klieman et al. | |
| 5,797,959 A | 8/1998 | Castro et al. | |
| 5,803,919 A | 9/1998 | Hart et al. | |
| 5,813,409 A | 9/1998 | Leahy et al. | |
| 5,814,058 A | 9/1998 | Carlson et al. | |
| 5,816,257 A | 10/1998 | Chin | |
| 5,827,319 A | 10/1998 | Carlson et al. | |
| 5,827,323 A | 10/1998 | Klieman et al. | |
| 5,836,960 A | 11/1998 | Kolesa et al. | |
| 5,840,078 A | 11/1998 | Yerys | |
| 5,853,395 A | 12/1998 | Crook et al. | |
| 5,865,807 A | 2/1999 | Blake, III | |
| 5,876,447 A | 3/1999 | Arnett | |
| 5,891,013 A | 4/1999 | Thompson | |
| 5,893,878 A | 4/1999 | Pierce | |
| 5,906,577 A | 5/1999 | Beane et al. | |
| 5,941,890 A | 8/1999 | Voegele et al. | |
| 5,947,922 A | 9/1999 | MacLeod | |
| 5,957,913 A | 9/1999 | de la Torre et al. | |
| 5,971,995 A | 10/1999 | Rousseau | |
| 5,977,431 A | 11/1999 | Knapp et al. | |
| 5,990,382 A | 11/1999 | Fox | |
| 6,007,561 A | 12/1999 | Bourque et al. | |
| 6,024,708 A | 2/2000 | Bales et al. | |
| 6,024,736 A | 2/2000 | de la Torre et al. | |
| 6,027,522 A | 2/2000 | Palmer | |
| 6,033,428 A | 3/2000 | Sardella | |
| 6,074,419 A | 6/2000 | Healy et al. | |
| 6,077,288 A | 6/2000 | Shimomura et al. | |
| 6,086,603 A | 7/2000 | Termin et al. | |
| 6,093,141 A | 7/2000 | Mosseri et al. | |
| 6,110,154 A | 8/2000 | Shimomura et al. | |
| 6,110,182 A | 8/2000 | Mowlai-Ashtiani | |
| 6,120,513 A | 9/2000 | Bailey et al. | |
| 6,123,689 A | 9/2000 | To et al. | |
| 6,126,671 A | 10/2000 | Richards et al. | |
| 6,132,385 A | 10/2000 | Vain | |
| 6,149,642 A | 11/2000 | Gerhart et al. | |
| 6,156,184 A | 12/2000 | Antonucci et al. | |
| 6,159,200 A | 12/2000 | Verdura et al. | |
| 6,162,196 A | 12/2000 | Hart et al. | |
| 6,165,184 A | 12/2000 | Verdura et al. | |
| 6,171,282 B1 | 1/2001 | Ragsdale | |
| 6,197,034 B1 | 3/2001 | Gvozdic et al. | |
| 6,217,555 B1 | 4/2001 | Hart et al. | |
| 6,220,248 B1 | 4/2001 | Voegele et al. | |
| 6,228,055 B1 | 5/2001 | Foerster et al. | |
| 6,245,052 B1 | 6/2001 | Orth et al. | |
| 6,248,062 B1 | 6/2001 | Adler et al. | |
| 6,258,069 B1 | 7/2001 | Carpentier et al. | |
| 6,258,102 B1 | 7/2001 | Pagedas | |
| 6,261,302 B1 | 7/2001 | Voegele et al. | |
| 6,264,599 B1 | 7/2001 | Slater et al. | |
| 6,290,705 B1 | 9/2001 | Chan et al. | |
| 6,293,966 B1 | 9/2001 | Frantzen | |
| 6,315,770 B1 | 11/2001 | de la Torre et al. | |
| 6,319,246 B1 | 11/2001 | de la Torre et al. | |
| 6,347,940 B1 | 2/2002 | Gordils Wallis | |
| 6,348,034 B1 | 2/2002 | Thompson | |
| 6,352,503 B1 | 3/2002 | Matsui et al. | |
| 6,400,979 B1 | 6/2002 | Stoianovici et al. | |
| 6,425,903 B1 | 7/2002 | Voegele | |
| 6,443,960 B1 | 9/2002 | Brabrand et al. | |
| 6,447,443 B1 | 9/2002 | Keogh et al. | |
| 6,447,489 B1 | 9/2002 | Peterson | |

| | | | | | | |
|---|---|---|---|---|---|---|
| 6,454,783 | B1 | 9/2002 | Piskun | 2004/0068291 A1 | 4/2004 | Suzuki |
| 6,458,077 | B1 | 10/2002 | Boebel et al. | 2004/0106942 A1 | 6/2004 | Taylor et al. |
| 6,471,714 | B1 | 10/2002 | Kim | 2004/0106986 A1 | 6/2004 | Andersson et al. |
| 6,485,467 | B1 | 11/2002 | Crook et al. | 2004/0138528 A1 | 7/2004 | Richter et al. |
| 6,551,270 | B1 | 4/2003 | Bimbo et al. | 2004/0147933 A1 | 7/2004 | McGovern |
| 6,551,282 | B1 | 4/2003 | Exline et al. | 2004/0167545 A1 | 8/2004 | Sadler et al. |
| 6,578,577 | B2 | 6/2003 | Bonadio et al. | 2004/0193212 A1 | 9/2004 | Taniguchi et al. |
| 6,579,304 | B1 | 6/2003 | Hart et al. | 2004/0215063 A1 | 10/2004 | Bonadio et al. |
| 6,589,167 | B1 | 7/2003 | Shimomura et al. | 2004/0225323 A1 | 11/2004 | Nagase et al. |
| 6,605,063 | B2 | 8/2003 | Bousquet | 2004/0230160 A1 | 11/2004 | Blanco |
| 6,613,068 | B2 | 9/2003 | Ouchi et al. | 2004/0230161 A1 | 11/2004 | Zeiner |
| 6,623,426 | B2 | 9/2003 | Bonadio et al. | 2004/0243108 A1 | 12/2004 | Suzuki |
| 6,634,883 | B2 | 10/2003 | Ranalli | 2004/0254426 A1 | 12/2004 | Wenchell |
| 6,663,641 | B1 | 12/2003 | Kovac et al. | 2004/0260198 A1 | 12/2004 | Rothberg et al. |
| 6,665,554 | B1 | 12/2003 | Charles et al. | 2004/0260337 A1 | 12/2004 | Freed |
| 6,666,854 | B1 | 12/2003 | Lange et al. | 2005/0020884 A1 | 1/2005 | Hart et al. |
| 6,669,674 | B1 | 12/2003 | Macoviak et al. | 2005/0033312 A1 | 2/2005 | Suzuki |
| 6,673,092 | B1 | 1/2004 | Bacher | 2005/0033342 A1 | 2/2005 | Hart et al. |
| 6,706,033 | B1 | 3/2004 | Martinez et al. | 2005/0033357 A1 | 2/2005 | Braun |
| 6,706,050 | B1 | 3/2004 | Giannadakis | 2005/0070754 A1* | 3/2005 | Nobis et al. ............... 600/16 |
| 6,725,083 | B1 | 4/2004 | Burbank et al. | 2005/0070764 A1* | 3/2005 | Nobis et al. ............... 600/131 |
| 6,764,473 | B2 | 7/2004 | Morton | 2005/0085842 A1 | 4/2005 | Eversull et al. |
| 6,766,186 | B1 | 7/2004 | Hoyns et al. | 2005/0107809 A1 | 5/2005 | Litscher et al. |
| 6,807,965 | B1 | 10/2004 | Hickle | 2005/0124912 A1 | 6/2005 | Griego et al. |
| 6,810,880 | B1 | 11/2004 | Jennings, Jr. et al. | 2005/0137609 A1 | 6/2005 | Guiraudon |
| 6,818,007 | B1 | 11/2004 | Dampney et al. | 2005/0148823 A1 | 7/2005 | Vaugh et al. |
| 6,821,247 | B2 | 11/2004 | Vierra et al. | 2005/0155611 A1 | 7/2005 | Vaugh et al. |
| 6,846,287 | B2 | 1/2005 | Bonadio et al. | 2005/0192483 A1 | 9/2005 | Bonadio et al. |
| RE38,702 | E | 2/2005 | Clement et al. | 2005/0209608 A1 | 9/2005 | O'Heeron |
| 6,908,430 | B2 | 6/2005 | Caldwell et al. | 2005/0222582 A1 | 10/2005 | Wenchell |
| 6,936,061 | B2 | 8/2005 | Sasaki | 2005/0228224 A1 | 10/2005 | Okada et al. |
| 6,939,296 | B2 | 9/2005 | Ewers et al. | 2005/0267419 A1 | 12/2005 | Smith |
| 6,945,932 | B1 | 9/2005 | Caldwell et al. | 2005/0273084 A1 | 12/2005 | Hinman et al. |
| 6,966,876 | B2 | 11/2005 | Irion et al. | 2005/0273132 A1 | 12/2005 | Shluzas et al. |
| 6,972,026 | B1 | 12/2005 | Caldwell et al. | 2005/0277946 A1 | 12/2005 | Greenhalgh |
| 6,994,712 | B1 | 2/2006 | Fisher et al. | 2006/0016853 A1 | 1/2006 | Racenet |
| 7,008,377 | B2 | 3/2006 | Beane et al. | 2006/0020241 A1 | 1/2006 | Piskun et al. |
| 7,014,628 | B2 | 3/2006 | Bousquet | 2006/0020281 A1 | 1/2006 | Smith |
| 7,021,173 | B2 | 4/2006 | Stoianovici et al. | 2006/0020287 A1 | 1/2006 | Lee et al. |
| 7,047,063 | B2 | 5/2006 | Burbank et al. | 2006/0042636 A1 | 3/2006 | Nalagatla et al. |
| 7,052,454 | B2 | 5/2006 | Taylor | 2006/0071432 A1 | 4/2006 | Staudner |
| 7,083,576 | B2 | 8/2006 | Zarins et al. | 2006/0149137 A1 | 7/2006 | Pingleton et al. |
| 7,083,626 | B2 | 8/2006 | Hart et al. | 2006/0212062 A1 | 9/2006 | Farascioni |
| 7,087,071 | B2 | 8/2006 | Nicholas et al. | 2006/0224129 A1 | 10/2006 | Beasley et al. |
| 7,118,528 | B1 | 10/2006 | Piskun | 2006/0224164 A1 | 10/2006 | Hart et al. |
| 7,147,650 | B2 | 12/2006 | Lee | 2006/0229501 A1 | 10/2006 | Jensen et al. |
| 7,163,510 | B2 | 1/2007 | Kahle et al. | 2006/0229641 A1 | 10/2006 | Gupta et al. |
| 7,201,734 | B2 | 4/2007 | Hickle | 2006/0241651 A1 | 10/2006 | Wilk |
| 7,208,005 | B2 | 4/2007 | Frecker et al. | 2006/0241671 A1 | 10/2006 | Greenhalgh |
| 7,214,185 | B1 | 5/2007 | Rosney et al. | 2006/0247499 A1 | 11/2006 | Butler et al. |
| 7,247,154 | B2 | 7/2007 | Hickle | 2006/0247500 A1 | 11/2006 | Voegele et al. |
| 7,311,661 | B2 | 12/2007 | Heinrich | 2006/0247516 A1 | 11/2006 | Hess et al. |
| 7,331,661 | B2 | 2/2008 | Silverbrook et al. | 2006/0247586 A1 | 11/2006 | Voegele et al. |
| 7,338,473 | B2 | 3/2008 | Campbell et al. | 2006/0247673 A1 | 11/2006 | Voegele et al. |
| 7,344,547 | B2 | 3/2008 | Piskun | 2006/0247678 A1 | 11/2006 | Weisenburgh et al. |
| 7,347,862 | B2 | 3/2008 | Layer | 2006/0258899 A1 | 11/2006 | Gill et al. |
| 7,416,533 | B2 | 8/2008 | Gellman et al. | 2006/0259071 A1 | 11/2006 | Nicholas et al. |
| 7,615,005 | B2 | 11/2009 | Stefanchik et al. | 2006/0259073 A1 | 11/2006 | Miyamoto et al. |
| 2001/0034528 | A1 | 10/2001 | Foerster et al. | 2006/0264706 A1 | 11/2006 | Piskun |
| 2001/0053510 | A1 | 12/2001 | Ranalli | 2006/0270911 A1 | 11/2006 | Voegele et al. |
| 2002/0007112 | A1 | 1/2002 | Rupp et al. | 2007/0049966 A1 | 3/2007 | Bonadio et al. |
| 2002/0026201 | A1 | 2/2002 | Foerster et al. | 2007/0060939 A1 | 3/2007 | Lancial et al. |
| 2002/0103434 | A1 | 8/2002 | Swanbom | 2007/0085232 A1 | 4/2007 | Brustad et al. |
| 2002/0156432 | A1 | 10/2002 | Racenet et al. | 2007/0088202 A1 | 4/2007 | Albrecht et al. |
| 2002/0173805 | A1 | 11/2002 | Matsuno et al. | 2007/0088277 A1 | 4/2007 | McGinley et al. |
| 2002/0193815 | A1 | 12/2002 | Foerster et al. | 2007/0106317 A1 | 5/2007 | Shelton et al. |
| 2003/0028179 | A1 | 2/2003 | Piskun | 2007/0118021 A1 | 5/2007 | Pokorney |
| 2003/0100814 | A1 | 5/2003 | Kindlein | 2007/0151566 A1 | 7/2007 | Kahle et al. |
| 2003/0109898 | A1 | 6/2003 | Schwarz et al. | 2007/0162072 A1 | 7/2007 | Nicholas et al. |
| 2003/0113540 | A1 | 6/2003 | Anderson et al. | 2007/0185453 A1 | 8/2007 | Michael et al. |
| 2003/0139756 | A1 | 7/2003 | Brustad | 2007/0208312 A1 | 9/2007 | Norton et al. |
| 2003/0206860 | A1 | 11/2003 | Bleyer et al. | 2007/0244358 A1 | 10/2007 | Lee |
| 2003/0208207 | A1 | 11/2003 | Layer | 2007/0250113 A1 | 10/2007 | Hegeman et al. |
| 2003/0225420 | A1 | 12/2003 | Wardle | 2007/0255219 A1 | 11/2007 | Vaugh et al. |
| 2003/0229338 | A1 | 12/2003 | Irion et al. | 2008/0027476 A1 | 1/2008 | Piskun |
| 2003/0236549 | A1 | 12/2003 | Bonadio et al. | 2008/0051739 A1 | 2/2008 | McFarlane |
| 2004/0015185 | A1 | 1/2004 | Ewers et al. | 2008/0065021 A1 | 3/2008 | Jenkins et al. |
| 2004/0023161 | A1 | 2/2004 | Yamaguchi et al. | 2008/0065107 A1 | 3/2008 | Larkin et al. |
| 2004/0024304 | A1 | 2/2004 | Foerster et al. | 2008/0065116 A1* | 3/2008 | Lee et al. ............... 606/142 |

| | | |
|---|---|---|
| 2008/0119821 A1 | 5/2008 | Agnihotri et al. |
| 2008/0147113 A1 | 6/2008 | Nobis et al. |
| 2008/0154299 A1 | 6/2008 | Livneh |
| 2008/0183044 A1 | 7/2008 | Colleran et al. |
| 2008/0255420 A1 | 10/2008 | Lee et al. |
| 2008/0255519 A1 | 10/2008 | Piskun et al. |
| 2008/0262492 A1 | 10/2008 | Lee |
| 2008/0269727 A1 | 10/2008 | Lee |
| 2008/0294191 A1 | 11/2008 | Lee |
| 2009/0005799 A1 | 1/2009 | Franer et al. |
| 2009/0062618 A1 | 3/2009 | Drew et al. |
| 2009/0088792 A1 | 4/2009 | Hoell, Jr. et al. |
| 2009/0171147 A1 | 7/2009 | Lee et al. |
| 2009/0206129 A1 | 8/2009 | Doll et al. |
| 2009/0306658 A1 | 12/2009 | Nobis et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0312060 A1 | 12/2010 | Widenhouse et al. |
| 2010/0312061 A1 | 12/2010 | Hess et al. |
| 2010/0312064 A1 | 12/2010 | Weisenburgh et al. |
| 2010/0312065 A1 | 12/2010 | Shelton et al. |
| 2011/0028793 A1 | 2/2011 | Martin et al. |
| 2011/0028794 A1 | 2/2011 | Widenhouse et al. |

FOREIGN PATENT DOCUMENTS

| | | |
|---|---|---|
| EP | 0646358 | 4/1995 |
| EP | 07766231 | 6/1997 |
| EP | 950376 | 10/1999 |
| EP | 0966924 | 12/1999 |
| EP | 0996925 | 5/2000 |
| EP | 1219251 | 7/2002 |
| EP | 1219252 | 7/2002 |
| EP | 1219253 | 7/2002 |
| EP | 1350476 | 10/2003 |
| EP | 1731105 | 12/2006 |
| FR | 2710270 | 3/1995 |
| JP | 2000033089 | 2/2000 |
| JP | 2006320750 | 11/2006 |
| WO | WO-96008897 | 9/1995 |
| WO | WO-9608208 A1 | 3/1996 |
| WO | WO-9712557 A1 | 4/1997 |
| WO | WO-9729709 A1 | 8/1997 |
| WO | WO-9735521 A1 | 10/1997 |
| WO | WO-9810712 A1 | 3/1998 |
| WO | WO-9903536 A1 | 1/1999 |
| WO | WO-0030592 A1 | 6/2000 |
| WO | WO-0032253 A1 | 6/2000 |
| WO | WO-0217810 A2 | 3/2002 |
| WO | WO-0239890 A2 | 5/2002 |
| WO | WO-0239918 A1 | 5/2002 |
| WO | WO-0258543 | 8/2002 |
| WO | WO-02094133 A1 | 11/2002 |
| WO | WO-03005890 A2 | 1/2003 |
| WO | WO-03067341 A2 | 8/2003 |
| WO | WO-03077730 A2 | 9/2003 |
| WO | WO-03091839 A2 | 11/2003 |
| WO | WO-2005087112 | 9/2005 |
| WO | WO-2005094432 A2 | 10/2005 |
| WO | WO-2006110733 A2 | 10/2006 |
| WO | WO-2007119232 A2 | 10/2007 |
| WO | WO-2008012787 A2 | 1/2008 |
| WO | WO-2008024502 A2 | 2/2008 |
| WO | WO-2009073577 A2 | 6/2009 |

OTHER PUBLICATIONS

"Adult Cardiac Surgical Instruments," from the website of Genesee BioMedical, Inc. (date of first publication unknown; downloaded May 3, 2007; 4 pages).

Advanced Surgical Concepts (ASC), 510(k) TriPort Laparoscopic Access Device, Dec. 26, 2007, 8 pages.

"Applied GelPort Advanced Access Device," by Applied Medical Resources Corporation (Nov. 2002).

"Applied GelPort System" by Applied Medical Resources Corporation (2004).

Ashida, R. et al., "Indocyanine Green is an Ideal Dye for Endoscopic Ultrasound-Guided Fine-Needle Tattooing of Pancreatic Tumors" *Endoscopy*, 38, pp. 190-192.

"Bard® Bi-Directional and Kelly-Wick Tunnelers—Instructions for Use," by Bard Peripheral Vascular (Apr. 2006).

Desai, M. et al., "Laprascopic and Robtoic Urology: Scarless single port transumbilical nephrectomy and pyeloplasty: first clinical report," Journal Compilation, 2008 BJU International, 101, 83-88.

"Hand Instruments," from the website of Olympus Surgical America (date of first publication unknown; downloaded May 3, 2007; 4 pages).

http://www.innomedic.de/en/products/innomotion_overview.php (Innomedic Products), accessed Oct. 24, 2006.

http://www.intuitivesurgical.com/products/index.aspx (Intuitive Surgical Products), accessed Oct. 24, 2006.

http://www.lap-laser.com/e/laser_m/prod/med.html (LAP Laser Application), accessed Oct. 24, 2006.

Ideas for Surgery.com, "Surgeon performs single-port laparoscopic surgery," dated Dec. 1, 2007.

"intrack XT—Low Profile Atraumatic Clamps," by Novare Surgical Systems, Inc. (2002).

Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).

Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.

Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.

Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.

"Pen Competitors," (date of first publication unknown but no later than May 15, 2007, date of citation in U.S. Appl. No. 11/398,985; 1 page).

Stoianovici, et al., "A Novel Mechanical Transmission Applied to Percutaneous Renal Access", DSC-vol. 61, Proceedings of the ASME Dynamic Systems and Control Division 1997.

*Twentieth Edition—Illustrations of Surgical Instruments*, by The Kny-Scheerer Compnay, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 339-3073, 3132, 3165, 3168-3169, 3208-3209, 3219 (Jul. 1915).

URobotics, Brady Urological Institute, Johns Hopkins Medical Institutions, "Z-Stage PAKY", date of publication unknown but no later than Oct. 26, 2006 (date of citation in U.S. Appl. No. 11/307,231).

URobotics, Brady Urological Institute, Johns Hopkins Medical Institutions, "PAKY Needle Driver," date of publication unknown but no later than Oct. 26, 2006 (date of citation in U.S. Appl. No. 11/307,231).

URobotics, Brady Urological Institute, Johns Hopkins Medical Institutions, "The RCM Robot", date of publication unknown but no later than Oct. 26, 2006 (date of citation in U.S. Appl. No. 11/307,231).

Webpage of Novare Surgical, Inc. featuring clamps (date of first publication unknown; downloaded Feb. 23, 2004; 1 page).

* cited by examiner

SELECTABLE HANDLE BIASING

FIELD

The present invention relates to methods and devices for performing surgical procedures, and in particular to methods and handle mechanisms for biasing end effectors.

BACKGROUND

In recent years, laparoscopic and endoscopic surgical procedures have become the standard for performing cholecystectomies, gastrostomies, appendectomies, and hernia repair, among many other procedures. Minimally invasive surgical instruments are used in these procedures to view, engage, and/or treat tissue within a body cavity or other surgical site to achieve a diagnostic or therapeutic effect. Some minimally invasive surgical instruments have user operated handles that allow a surgeon to manipulate an end effector of the instrument, such as opposed clamping or stapling jaws, to grasp, fasten, or otherwise engage tissue. There are various styles of handles, but generally many user operated handles are configured such that the handles and the opposed jaws are biased to an open configuration. The handle must therefore be squeezed by a user to close the jaws. When the handle is released by the user, the jaws will move to the open configuration because of the biasing. While this configuration has many benefits, in some situations such as during fine dissection, uncontrolled opening of the jaws is undesirable because it could cause damage to surrounding tissue. It would therefore be advantageous for a user to be able to choose whether the jaws are biased open, closed, or to a neutral configuration so that the device is suitable for a wider variety of surgical procedures.

Accordingly, there is a need for improved methods and devices having user selected configurations.

SUMMARY

The devices and methods disclosed herein generally involve elongate surgical instruments that include a biasing mechanism effective to selectively bias an end effector to one of an open position and a closed position. While this can be accomplished in many ways, in one aspect, a surgical instrument is provided and can include an elongate shaft having opposed jaws at a distal end thereof. A handle housing can be disposed at a proximal end of the elongate shaft and it can have a trigger configured to pivot to open and close the opposed jaws. A biasing switch can be disposed in and/or on the handle housing and can be selectively movable between a first configuration in which the opposed jaws are biased to an open position, and a second configuration in which the opposed jaws are biased to a closed position.

The biasing switch can have any configuration effective to selectively bias the opposed jaws, however, in some embodiments, the biasing switch can include an opening spring and a closing spring. The opening spring can be configured to bias the opposed jaws to the open position, and the closing spring can be configured to bias the opposed jaws to the closed position. The biasing switch can further include a lever disposed in the handle housing and positioned between the opening and closing springs. The lever can be configured to selectively compress the opening spring to bias the opposed jaws to the open configuration and to compress the closing spring to bias the opposed jaws to the closed position. In some embodiments, the biasing switch can include a neutral configuration in which the opposed jaws are unbiased. In other embodiments, the biasing switch can include a plurality of positions, for example, a continuous range of positions, between the neutral configuration and the open and closed configurations.

In one embodiment, the closing spring can be disposed between the lever and a proximal bushing coupled to an actuating member extending through the elongate shaft and coupled to the opposed jaws. Similarly, the opening spring can be disposed between the lever and a distal bushing coupled to the actuating member. Longitudinal movement of the actuating member relative to the elongate shaft can be effective to move the opposed jaws between the open and closed positions.

In another embodiment, the surgical instrument can include an actuating member extending through the elongate shaft and coupled to the biasing switch and the opposed jaws. While the actuating member can have various configuration, in some embodiments, it can be movable longitudinally relative to the elongate shaft to move the jaws between the open and closed positions. The handle housing can have various forms known in the art and can include a stationary handle that is pivotally coupled to the trigger and that extends generally parallel to the trigger when the trigger is in a closed position. Pivotal movement of the trigger toward the stationary handle is effective to close the opposed jaws, and pivotal movement of the trigger away from the stationary handle is effective to open the opposed jaws. A person having ordinary skill in the art will appreciate that during such pivotable movement only one or both of the trigger and the stationary handle can move to open and close the opposed jaws.

In other aspects, a surgical device is provided and can include a handle and an elongate shaft extending from a distal end of the handle. Opposed jaws can be coupled to a distal end of the elongate shaft and can be movable between an open position and a closed position. In some embodiments, an actuating member can extend through the elongate shaft and can couple to the opposed jaws such that movement of the actuating member in a first direction is configured to move the opposed jaws to the open position, and movement of the actuating member in a second opposite direction is configured to move the opposed jaws to the closed position.

The surgical device can also include a biasing element disposed within the handle and coupled to the actuating member. In some embodiments, the biasing element can be selectively movable between a first position in which the biasing element biases the actuating member in the first direction, and a second position in which the biasing element biases the actuating member in the second direction. The biasing element can also have a neutral configuration in which the actuating member is unbiased.

The handle can have many configurations. For example, the handle can include first and second elongate members having proximal and distal ends. The elongate shaft can extend distally from the distal end of the first elongate member, and the proximal end of the second elongate member can be pivotally coupled to the proximal end of the first elongate member. In addition, pivotal movement of the second elongate member relative to the first elongate member can be effective to move the actuating member in the first and second directions. The first and second elongate members can be pivotally movable between an open position, in which the distal end of the second elongate member is spaced a distance apart from the distal end of the first elongate member, and a closed position in which longitudinal axes of the first and second elongate members extend substantially parallel to one another.

While there are many ways possible to accomplish selective movement of the biasing element, in one embodiment a lever can be disposed on and/or in the handle and it can be coupled to the biasing element for moving the biasing element between the first and second positions. The biasing element can also include a first spring configured to be compressed against a distal stop to bias the actuating member in the first direction. Further, the biasing element can include a second spring configured to be compressed against a proximal stop to bias the actuating member in the second direction. The handle can optionally include a lever disposed thereon and extending between the first and second springs such that the lever is configured to selectively compress one of the first and second springs. For example, the lever can be movable in a first direction to compress the first spring and in a second, opposite direction to compress the second spring.

Surgical methods are also provided and in one embodiment, a method can include positioning an end effector on a distal end of an elongate shaft of a surgical device in a body cavity. The method can also include moving a biasing switch on a handle of the surgical device to one of a first position in which the biasing switch biases the end effector to a first configuration, and a second position in which the biasing switch biases the end effector to a second configuration. Actuating a trigger on the handle can be effective to move the end effector from the first configuration to the second configuration. In some embodiments, the biasing switch on the handle can be moved to the other one of the first and second positions. The end effector can have many configurations, for example, the end effector can be opposed jaws that are open in the first configuration and closed in the second configuration.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. A number of problems with conventional methods and devices are noted in the "background" section of this application and the methods and devices disclosed herein may address one or more of these problems. By describing these problems, no admission as to their knowledge in the art is intended.

In general, the present invention relates to surgical devices provided for use in various surgical procedures. In some embodiments, the surgical devices can include a handle housing and an elongate shaft having opposed jaws disposed at a distal end thereof. The handle housing can have a handle portion and a trigger configured to pivot relative to the handle portion to open and close the opposed jaws. A biasing switch can generally be disposed in and/or on the handle housing and it can be selectively movable between a first configuration in which the opposed jaws are biased to an open position, and a second configuration in which the opposed jaws are biased to a closed position. The biasing switch can also have a neutral position where no biasing force is applied. A person skilled in the art will appreciate that, while methods and devices are described herein in connection with minimally invasive laparoscopic or endoscopic procedures, the methods and devices can be used in almost any procedure, such as open surgical procedures, and in almost any part of a human or animal body. By way of non-limiting example, the devices and methods disclosed herein can be used in the thoracic cavity, pelvic cavity, cranial cavity and/or any of the body's natural orifices.

Figure 1A:
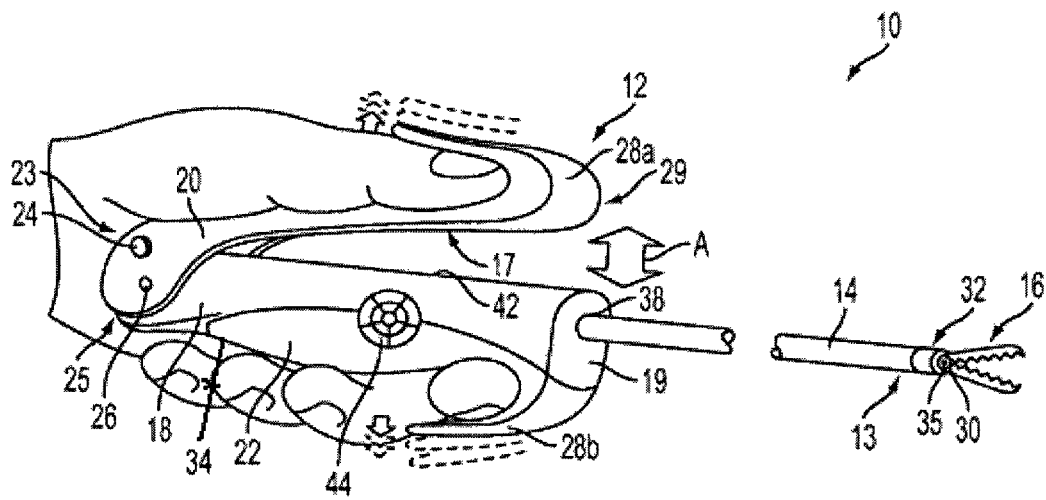
FIG. 1A is a perspective view of one embodiment of surgical device having a biasing mechanism disposed therein for biasing opposed jaws of the device to one of an open and closed position.
Figure 2A:
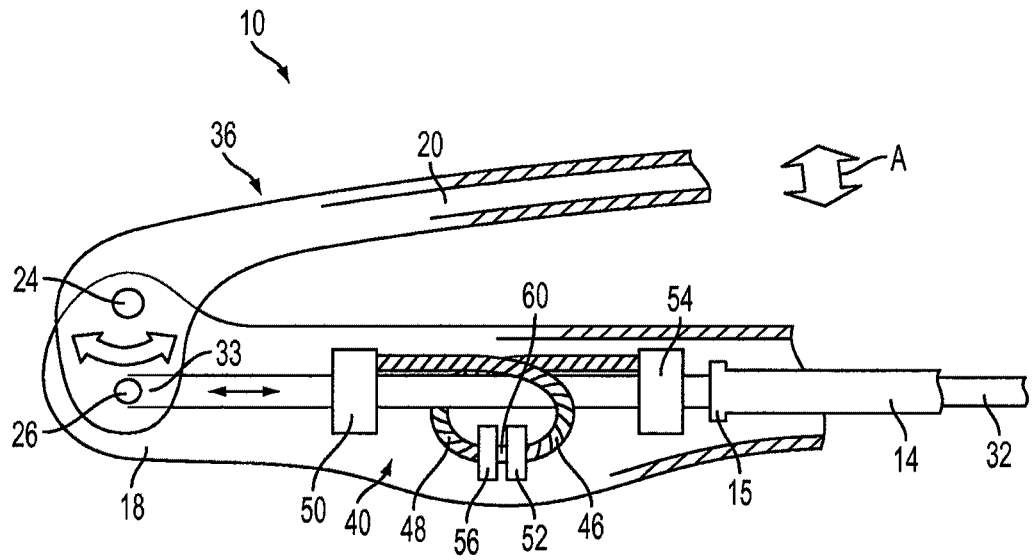
FIG. 2A is a cross-sectional view of the surgical device of FIG. 1A illustrating opening and closing springs for biasing the surgical device to one of an open and closed position.

FIG. 1A illustrates one exemplary embodiment of a surgical device 10. As shown, the device 10 can include a handle housing 12 having an elongate shaft 14 extending distally therefrom. The elongate shaft 14 can have a distal end 13 disposed outside of the handle housing 12 and a proximal end 15 disposed inside the handle housing 12, as shown in FIG. 2A. The elongate shaft 14 can have a hollow lumen extending therethrough between its proximal and distal ends 15, 13 along a central longitudinal axis of the elongate shaft 14. As shown in FIG. 2A, the elongate shaft 14 can extend partially into the handle housing 12 and can fit within an opening 38 formed in the shroud of the handle housing 12. In the illustrated embodiment, the elongate shaft 14 only extends into a distal portion of the handle housing 12, but it will be appreciated by a person skilled in the art that the elongate shaft 14 can extend any distance into the handle housing 12, including to the proximal-most portion thereof.

As will be appreciated by those having ordinary skill in the art, an end effector can be formed on the distal end 13 of the elongate shaft 14. The end effector can be any surgical tool needed for a particular procedure including, but not limited to, one or more graspers, dissectors, babcocks, scissors, staplers, piercing members, clamping members, suturing members, electrocautery members, ultrasonic members, bipolar radio-frequency, etc. In the illustrated embodiment of FIG. 1A, two opposed grasping jaws 16 are disposed on the distal end 13 of the elongate shaft 14. The opposed jaws 16 can be moved between an open configuration (shown in FIG. 1A) and a closed configuration, as will be described in more detail below.

The handle housing 12 can generally be any handle housing type known in the art, including scissor style housings, stapler housings, pistol grip, and in-line grasper/dissector/babcocks, Kelly clamp handles, ultrasonic or radio-frequency control handles, among others. In the illustrated embodiment, the handle housing 12 is an in-line handle housing that can be formed of any material that exhibits sufficient rigidity and suitability for surgical applications. For example, at least a portion of the handle housing 12, if not all of the housing 12, can be formed from a plastic or metal. In some embodiments, the handle housing 12 can be formed of two or more different materials to ensure appropriate gripping surfaces for a user. For example, as shown in FIG. 1A, at least a portion 22 of the handle housing 12 can be formed of and/or covered with an elastomeric material to provide an appropriate gripping surface for a user. The handle housing 12 can be designed to have a low profile and it can have a substantially hollow interior for holding the various components of the device 10, as will described in more detail below.

The handle housing 12 can include features capable of opening and closing the opposed jaws 16. In the illustrated embodiment, the handle housing 12 is formed from a stationary handle 18 and a movable trigger 20. The trigger 20 is generally elongate, with a width and a length sufficient to facilitate grasping by a user's finger, thumb, or entire hand, although as will be appreciated by those having ordinary skill in the art, the trigger 20 can have any shape or configuration as desired or as is necessary. The stationary handle 18 can have many configurations and can generally have a size and shape sufficient to retain the various distal actuating and biasing components associated with the device 10 that will be described in more detail below. The handle 18 can also have various configurations, but in the illustrated embodiment it is generally elongate with a width and a length sufficient to facilitate grasping by a user's hand. The handle 18 can have an opening 38 formed in its distal-most end 19 for receiving the elongate shaft 14. An interior surface 42 of the stationary handle 18 that is in facing relationship with an interior surface 17 of the trigger 20 can be substantially flat while an exterior surface 34 of the stationary handle 18 can be contoured to provide an appropriate gripping surface for a user's hand. A person having ordinary skill in the art will appreciate the variety of shapes and configurations the handle 18 can have.

The trigger 20 can be movably coupled to the handle 18 at a variety of locations, but in the illustrated embodiment a proximal end 23 of the trigger 20 is pivotally coupled to a proximal end 25 of the stationary handle 18 such that the trigger 20 and the stationary handle 18 can extend substantially parallel to one another when the rigger 18 is pivoted toward the stationary handle 18. As shown, the trigger 20 and the stationary handle 18 are coupled at a fixed pivot point 24 and at a movable pivot 26. The trigger 20 can have an open configuration, shown in FIG. 1A, in which a distal end 29 of the trigger 20 is a distance away from the distal end 19 of the handle 18. The trigger 20 can be moved from the open configuration to a closed configuration by squeezing the trigger 20 toward the handle 18 in the direction shown by arrow "A" such that the distance between the distal end 29 of the trigger 20 and the distal end 19 of the handle 18 is decreased. As will be appreciated by those of ordinary skill in the art, the handle 12 can be configured for movement opposite to that noted above. For example, the distal end 19 of the handle 18 and the distal end 29 of the trigger 20 can be pivotally coupled together such that the proximal end 23 of the trigger 20 and the proximal end 25 of the handle 18 move relative to one another.

Figure 1B:
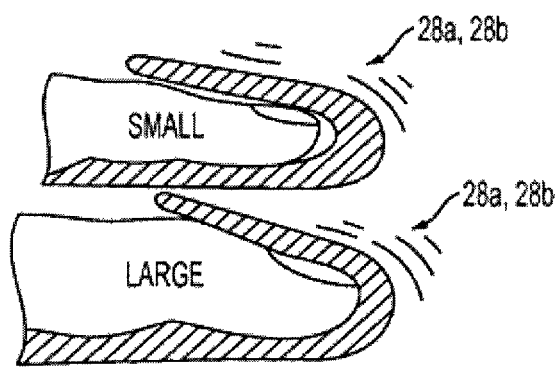
FIG. 1B is a side view of one embodiment of elastomeric finger hooks for use with the surgical device of FIG. 1A.

In some embodiments, one or more handles or hooks can be provided on the handle housing 12 to enable a user to more easily open the opposed jaws 16. Referring to FIGS. 1A and 1B, in one embodiment, a thumb hook 28a can be disposed on the trigger 20 and a finger hook 28b can be disposed on the handle 18. The thumb and finger hooks 28a, 28b can be in the form of a u-shaped hook extending proximally with an opening defined for receiving a user's thumb or finger. The thumb and finger hooks 28a, 28b can be formed of any suitable material known in the art such as an elastomeric material. A substantially flexible elastomeric material allows users with various sized fingers to use the same device. The elastomeric material can flex and deform to allow both large and small fingers to fit within the opening of the hooks 28a, 28b. Thus if needed, by using one hand, a user can pull the trigger 20 away from the handle 18 to open the opposed jaws 16.

Figure 2B:
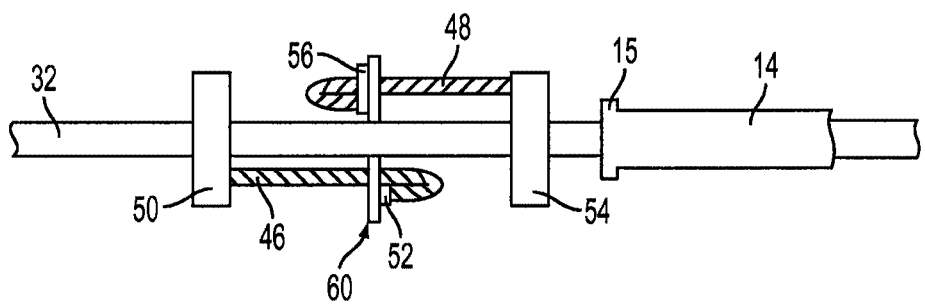
FIG. 2B is a top view of the biasing mechanism of FIG. 1A.
Figure 4:
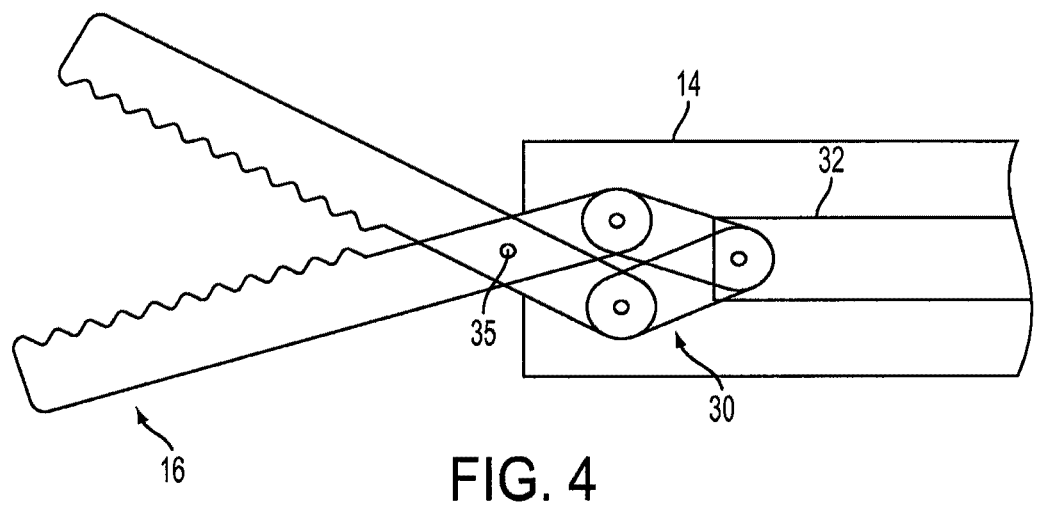
FIG. 4 is a side view of exemplary linkage mechanism connecting the actuating rod with the opposed jaws of the surgical device of FIG. 1A.

While there are many ways for the handle 18 and the trigger 20 to open and close the opposed jaws 16, in the embodiment illustrated in FIGS. 1A, 2A, and 2B, a drive-rod or actuator 32 extends between the opposed jaws 16 and the handle 18 and the trigger 20. The actuator 32 can be effective to move the opposed jaws 16 between open and closed configurations. The actuator 32 can extend through the lumen in the elongate shaft 14 such that the elongate shaft 14 circumferentially encloses at least a portion of, if not all of, the actuator 32. The actuator 32 can have a proximal end 33 coupled to and/or integrally formed with the movable pivot 26, which can be for example, a ball and socket joint. A distal end, shown in FIG. 4, can be coupled to the opposed jaws 16. The opposed jaws 16 can be coupled to the actuator 32 in a variety of ways. In the embodiment shown in FIG. 4, an articulating linkage 30 is provided between the actuator 32 and a pivot 35 of the opposed jaws 16 to permit opening and closing of the opposed jaws 16 with respect to the elongate shaft 14 in response to movement of the actuator 32, as will be described in more detail below.

In some embodiments, the device 10 can have a mechanism generally capable of selectively biasing the opposed jaws 16 to one of an open configuration or a closed configuration. If the opposed jaws 16 are biased to the open configuration, the trigger 20 will also be biased open (i.e., away from handle 18), and a user will be required to apply an inwardly directed force against the biasing resistance to move the trigger 20 toward the handle 18 to close the opposed jaws 16. If the user removes this "squeezing" force from the trigger 20 and the handle 18, the biasing mechanism will cause the trigger 20 to move away from the handle 18, thereby allowing the opposed jaws 16 to open. If the opposed jaws 16 are biased closed, the trigger 20 will also be biased closed (i.e., closer to the handle 18), and a user will be required to apply an outwardly directed force to the trigger 20 via the finger hooks 28a, 28b against the biasing resistance to open the opposed jaws 16. If a user releases this opening force, the biasing mechanism will cause the trigger 20 to move toward the handle 18, thereby allowing the opposed jaws 16 to close.

The device 10 can also have a neutral position in which the opposed jaws 16 and the trigger 20 are not biased to an open or closed configuration. The trigger 20 and the opposed jaws 16 will therefore stay in whatever position they are placed in by a user. For example, when the biasing mechanism is in the neutral configuration, if a user moves the trigger 20 toward the handle 18 to cause the opposed jaws 16 to close, the trigger 20 and the opposed jaws 16 can remain in the closed configuration even if the trigger 20 is released by the user. Likewise, if a user moves the trigger 20 away from the handle 18 to cause the opposed jaws 16 to open, the trigger 20 and the opposed jaws 16 can remain in the open configuration even if the trigger 20 is released by the user. As will be appreciated by those skilled in the art, this also applies to any position of the trigger 20 and the opposed jaws 16 between the fully open and fully closed configurations. The trigger 20 and the opposed jaws 16 can selectively remain in any desired position between the fully open and fully closed configurations when the biasing mechanism is in the neutral configuration.

The biasing mechanism can have a variety of configurations for accomplishing the various exemplary biasing arrangements noted above. In an embodiment illustrated in FIGS. 2A and 2B, a biasing mechanism 40 is provided having a plurality of biasing elements for selectively biasing the actuator 32, and thereby the trigger 20 and the opposed jaws 16, to one of an open and closed configuration. Alternatively, the biasing mechanism can provide no biasing to the actuator 32 such that the device 10 is in the neutral configuration as described above.

The biasing elements can take the form of any spring-like element known in the art, including, but not limited to, compression springs, leaf springs, cantilever springs, hairsprings, v-springs, torsion springs, negator springs, wave springs, etc. In the embodiment illustrated in FIGS. 2A-3 however, the biasing elements are in the form of compression springs. In particular, an opening spring 46 is provided within the handle 18. When the opening spring 46 is compressed, it can bias the actuator 32 proximally to the open configuration such that the trigger 20 and the opposed jaws 16 are also biased to the open configuration. A closing spring 48 is also provided within the handle 18. When the closing spring 48 is compressed, it can bias the actuator 32 distally to the closed configuration such that the trigger 20 and the opposed jaws 16 are also biased to the closed configuration.

While the opening spring 46 can couple to the actuator 32 using various techniques to provide a biasing force, in the illustrated embodiment, the opening spring 46 is coupled between a proximal stop or bushing 50 and an opening compression switch 52. The opening compression switch 52 can be a substantially rectangular or circular block member disposed offset from, e.g., below or inferior to the actuator 32 as shown, although as will be appreciated by those having ordinary skill in the art, it can be positioned in any suitable place within the handle 18. The opening spring 46 can be disposed within a semi-circular shroud formed within the inside wall of the handle 18 (not shown). One end of the opening spring 46 can couple to the opening compression switch 52, and the spring 46 can curl around in a semi-circle within the shroud, and the opposite end can couple to the proximal bushing 50. The proximal bushing 50 can be a substantially cylindrical sleeve-like member that fits circumferentially around and couples to the actuator 32 such that movement of the proximal bushing 50 results in corresponding movement of the actuator 32. The opening spring 46 can be fixedly coupled to the opening compression switch 52 and the proximal bushing 50 by any mechanism know in the art, including but not limited to, welding, being integrally formed therewith, a fastener, adhesive, an interference fit, etc. The proximal bushing 50 can be fixedly coupled to the actuator 32 by any mechanism known in the art, including, but not limited to, welding, being integrally formed therewith, a fastener, adhesive, an interference fit, etc.

Similarly, the closing spring 48 can be coupled to a distal bushing 54 and a closing compression switch 56. The closing spring 48 can be disposed within a semi-circular shroud formed within the inside wall of the handle 18, for example, on a side of the handle 18 opposite to that of the opening spring 46. The closing compression switch 56 can be a substantially rectangular or circular block member disposed adjacent to, e.g., below or inferior to the actuator 32 as shown, although it can be disposed in any appropriate position within the handle 18. One end of the closing spring 48 can couple to the closing compression switch 56, the closing spring 48 can curl around in a semi-circle within the shroud, and the opposite end can couple to the distal bushing 54. The closing spring 48 can be fixedly coupled to the closing compression switch 56 and the distal bushing 54 by any mechanism know in the art, including but not limited to, welding, being integrally formed therewith, a fastener, adhesive, an interference fit, etc. The distal bushing 54 can be a substantially cylindrical sleeve-like member that fits circumferentially around and couples to the actuator 32 at a position distal to the proximal bushing 50. Movement of the distal bushing 54 results in corresponding movement of the actuator 32. The distal bushing 54 can be fixedly coupled to the actuator 32 by any mechanism known in the art, including, but not limited to, welding, being integrally formed therewith, a fastener, adhesive, an interference fit, etc.

Figure 2C:
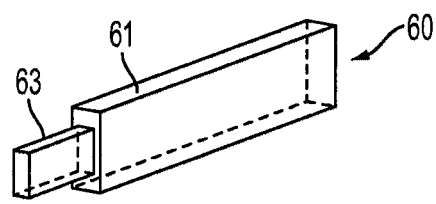
FIG. 2C is a perspective view of an exemplary lever associated with the biasing mechanism of FIG. 1A.

The biasing mechanism can also include a boss or lever 60, illustrated in FIG. 2A-2C, that can be disposed within the handle 18 between the opening and closing compression switches 52, 56. The lever 60 can include an elongate member 61 that extends across a width of the handle 18 such that it contacts a side of the opening and closing compression switches 52, 56 not coupled to the opening and closing springs 46, 48. For example, the lever 60 can contact the side of the opening compression switch 52 that is not coupled to the opening spring 46 on one side of the handle 18. The lever 60 can extend from the closing compression switch 52 across a center portion of the handle 18 to contact the closing compression switch 56 on the opposite side of the handle 18. Similarly to the opening compression switch 52, the lever can contact a side of the closing compression switch 56 that is not coupled to the closing spring 48.

Figure 3A:
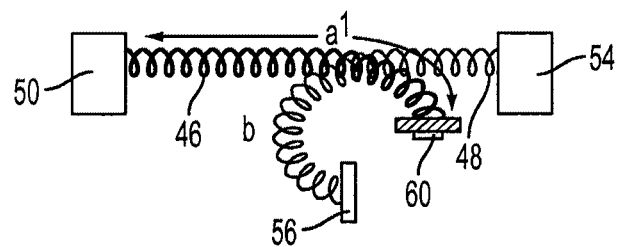
FIG. 3A is a side view of the biasing mechanism of FIG. 1A in a biased closed configuration.

In one embodiment, the lever 60 can also include a tang 63 that can extend from one end of the elongate member 61 and into a rotatable dial 44 illustrated in FIG. 1A. As will be appreciated by those having ordinary skill in the art, the tang 63 can have a smaller length, width, and height than the elongate member 61 as shown, or it can have a larger length, width, and height if needed. In some embodiments, the elongate member 61 and the tang 63 are a single component having the same length, width, and height. The lever 60 can be fixedly coupled to the biasing dial 44 by any mechanism known in the art such that movement of the biasing dial 44 results in corresponding movement of the lever 60. Such a mechanism can include, but is not limited to, welding, being integrally formed therewith, a fastener, adhesive, an interference fit, etc. In this way, rotation of the biasing dial 44 results in corresponding movement of the lever 60 to bias the device 10 in one of a closed configuration, an open configuration, or a neutral configuration. For example, referring to FIGS. 2A-3C, in use, rotation of the dial 44 in a counter-clockwise direction as shown in FIG. 3A causes corresponding rotation of the lever 60 in the counter-clockwise direction. As the lever 60 rotates in the counter-clockwise direction, it presses against the closing compression switch 52, causing it to move within its shroud to compress the closing spring 48 against the proximal bushing 50. Compression of the closing spring 48 against the proximal bushing 50 causes longitudinal movement of the proximal bushing 50 in the proximal direction. This in turn causes longitudinal movement of the actuator 32 in the proximal direction, which functions to bias the opposed jaws 16 and the trigger 20 to the closed configuration. Because the lever 60 is compressing the closing compression switch 52, it is no longer in engagement with the opening compression switch 56. The opening compression switch 56 and the opening spring 46 are therefore not restrained and are thus free to move within their bushing in the counter-clockwise direction by whatever amount necessary such that the distal bushing 54 can move with the actuator 32 in the proximal direction (since it is coupled thereto).

Figure 5:
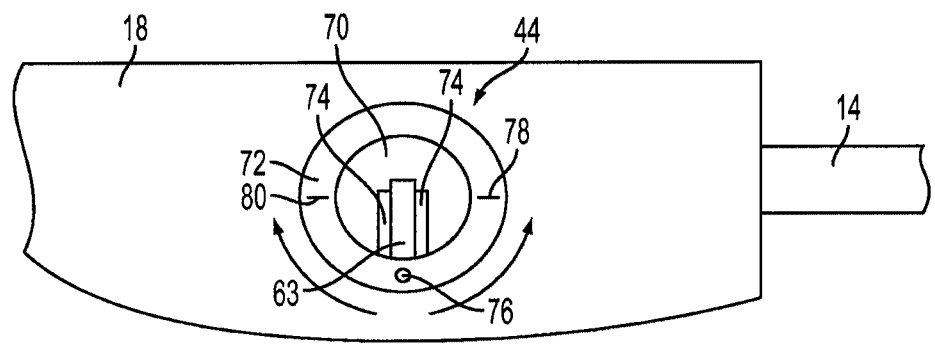
FIG. 5 is a partial cross-sectional view of an exemplary biasing switch for operating the biasing mechanism of FIG. 1A.

Once the closing spring 48 is fully compressed by the lever 60, and thus the opposed jaws 16 and the trigger 20 are in the fully closed configuration, the dial 44 and/or the lever 60 can engage a ratchet-style mechanism or other frictional engagement mechanism that functions to retain the lever 60 in its position. For example, as shown in FIG. 5, the dial 44 can include an inner ring 70 and outer ring 72. The inner ring 70 can include an opening and/or two protrusions 74 that can receive the tang 63 of the lever 60 so that movement of the dial 44 causes corresponding movement of the tang 63, and thereby movement of the opening and closing springs 46, 48. The outer ring 72 can include a protrusion 76 that can be configured to rotate with the dial 44 to engage detents 78 if the dial 44 is rotated counter-clockwise to hold the biasing mechanism 40 in the closed configuration. Likewise, if the dial 44 is rotated clockwise, the protrusion 76 can engage a detent 80 to hold the biasing mechanism 40 in the open configuration. In this way, the trigger 20, the opposed jaws 16, and the actuator 32 are biased to the closed configuration by the biasing mechanism. To open the opposed jaws 16, a user must apply an opening force against the closing biasing force by pulling the trigger 20 away from the stationary handle 18, e.g., using the finger hooks 28a, 28b. Once this opening force is removed, the trigger 20, the opposed jaws 16, and the actuator 32 will return to the closed configuration due to the biasing.

Figure 3B:
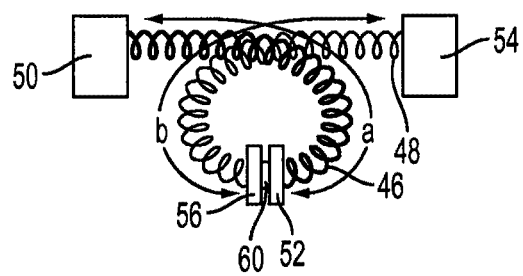
FIG. 3B is a side view of the biasing mechanism of FIG. 1A in a neutral configuration.
Figure 3C:
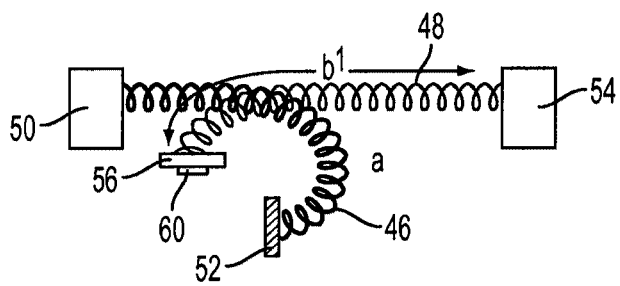
FIG. 3C is a side view of the biasing mechanism of FIG. 1A in a biased open configuration.

Likewise, rotation of the dial 44 in a clockwise direction as shown in FIG. 3C causes corresponding rotation of the lever 60 in the clockwise direction. As the lever 60 rotates in the clockwise direction, it presses against the opening compression switch 56, causing it to move within its shroud to compress the opening spring 46 against the distal bushing 54. Compression of the opening spring 46 against the distal bushing 54 causes longitudinal movement of the distal bushing 54 in the distal direction. This in turn causes longitudinal movement of the actuator 32 in the distal direction, which functions to bias the opposed jaws 16 and the trigger 20 to the open configuration. Because the lever 60 is compressing the opening compression switch 56, it is no longer in engagement with the closing compression switch 52. The closing compression switch 52 and the closing spring 48 are therefore not restrained and are thus free to move within their bushing in the clockwise direction by whatever amount necessary such that the proximal bushing 50 can move with the actuator 32 in the distal direction (since it is coupled thereto).

Once the opening spring 46 is fully compressed by the lever 60, and thus the opposed jaws 16 and the trigger 20 are biased to the fully open configuration, the dial 44 and/or the lever 60 can engage the ratchet-style mechanism, such as that illustrated in FIG. 5, or other frictional engagement mechanism that functions to retain the lever 60 in its position. In this way, the trigger 20, the opposed jaws 16, and the actuator 32 are biased to the open configuration by the biasing mechanism. To close the opposed jaws 16, a user must apply a squeezing, closing force to the handle housing 12 against the opening biasing force. Once the closing force is removed, the trigger 20, the opposed jaws 16, and the actuator 32 will return to the open configuration because of the biasing.

When the rotatable dial 44, and thus the lever 60, is in a neutral, non-rotated configuration shown in FIG. 3B, there is no biasing applied to the actuator 32. Thus, as the trigger 20 is opened or closed to move the opposed jaws 16 to the open or closed configuration, the actuator 32, the trigger 20, and the opposed jaws 16 can stay in their current position when the opening or closing force is removed. In addition, the trigger 20 can be moved to any position between the fully open and fully closed configurations, for example, partially open or partially closed positions, and the opposed jaws 16 can stay in that particular position.

In the above-described embodiment and as shown in FIG. 5, the dial 44 and the lever 60 can generally be selectively movable between three discrete positions: neutral, biased open, or biased closed. In some embodiments, the rotatable dial 44 can be movable between a plurality of discrete positions and/or a continuous range of positions. For example, any rotation of the dial 44 can be effective to bias the actuator 32 by a corresponding amount such that the amount of biasing can be controlled. If a user wishes to apply only a small amount of opening bias, the dial 44 can be rotated by a small amount until the desired biasing resistance is attained. Likewise, if a user wishes to apply a medium amount of closing bias, the dial 44 can be rotated by a medium amount until the desired biasing resistance is attained. Furthermore, during use, the biasing resistance can be adjusted as needed using the dial 44 in a way similar to a tuning dial. The opening biasing resistance can be increased from neutral up to a maximum opening biasing resistance. Likewise, the closing biasing resistance can be increased from neutral up to a maximum closing biasing resistance.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument, comprising:
an elongate shaft having opposed jaws at a distal end thereof;
a handle housing coupled to a proximal end of the elongate shaft and having a trigger configured to pivot to open and close the opposed jaws; and
a biasing switch disposed in the handle housing and selectively movable between a first configuration in which the opposed jaws are biased to an open position such that pivoting the trigger toward the handle housing closes the jaws, and a second configuration in which the opposed jaws are biased to a closed position such that pivoting the trigger away from the handle housing opens the jaws.

2. The surgical instrument of claim 1, wherein the biasing switch includes an opening spring and a closing spring, the opening spring being configured to bias the opposed jaws to the open position and the closing spring being configured bias the opposed jaws to the closed position.

3. The surgical instrument of claim 2, wherein the biasing switch further includes a lever disposed in the handle housing and positioned between the opening and closing springs, the lever being configured to compress the opening spring to bias the opposed jaws to the open configuration and to compress the closing spring to bias the opposed jaws to the closed position.

4. The surgical instrument of claim 3, wherein the closing spring is disposed between the lever and a proximal bushing coupled to an actuating member extending through the elongate shaft and coupled to the opposed jaws, and the opening spring is disposed between the lever and a distal bushing coupled to the actuating member.

5. The surgical instrument of claim 4, where longitudinal movement of the actuating member relative to the elongate shaft is effective to move the opposed jaws between the open and closed positions.

6. The surgical instrument of claim 1, further comprising an actuating member extending through the elongate shaft and coupled to the biasing switch and the opposed jaws, the actuating member being movable longitudinally relative to the elongate shaft to move the jaws between the open and closed positions.

7. The surgical instrument of claim 1, wherein the handle housing includes a stationary handle that is pivotally coupled to the trigger and that extends generally parallel to the trigger when the trigger is in a closed position.

8. The surgical instrument of claim 1, wherein the biasing switch includes a neutral configuration in which the opposed jaws are unbiased.

9. A surgical device, comprising:
a handle having first and second elongate members;
an elongate shaft extending from a distal end of the handle;
opposed jaws coupled to a distal end of the elongate shaft and movable between an open position and a closed position;
an actuating member extending through the elongate shaft and coupled to the opposed jaws, wherein movement of the actuating member in a first direction is configured to move the opposed jaws to the open position, and movement of the actuating member in a second opposite direction is configured to move the opposed jaws to the closed position; and
a biasing element disposed within the handle and coupled to the actuating member, the biasing element being selectively movable between a first position in which the biasing element biases the actuating member in the first direction, and a second position in which the biasing element biases the actuating member in the second direction;
wherein when the biasing element is in the first position, pivoting the distal end of the second elongate member away from the first elongate member opens the opposed jaws, and when the biasing element is in the second position, pivoting the distal end of the second elongate member toward the first elongate member closes the opposed jaws.

10. The surgical device of claim 9, wherein the biasing element has a neutral configuration in which the actuating member is unbiased.

11. The surgical device of claim 9, further comprising a lever disposed on the handle and coupled to the biasing element for moving the biasing element between the first and second positions.

12. The surgical device of claim 9, wherein the handle comprises first and second elongate members having proximal and distal ends, the elongate shaft extending distally from the distal end of the first elongate member, and the proximal end of the second elongate member being pivotally coupled to the proximal end of the first elongate member.

13. The surgical device of claim 12, wherein pivotal movement of the second elongate member relative to the first elongate member is effective to move the actuating member in the first and second directions.

14. The surgical device of claim 12, wherein the first and second elongate members are pivotally movable between an open position, in which the distal end of the second elongate member is spaced a distance apart from the distal end of the first elongate member, and a closed position in which longitudinal axes of the first and second elongate members extend substantially parallel to one another.

15. The surgical device of claim 9, wherein the biasing element includes a first spring configured to be compressed against a distal stop to bias the actuating member in the first direction, and a second spring configured to be compressed against a proximal stop to bias the actuating member in the second direction.

16. The surgical device of claim 15, wherein the handle includes a lever disposed thereon and extending between the first and second springs such that the lever is configured to selectively compress one of the first and second springs.

17. The surgical device of claim 16, wherein the lever is movable in a first direction to compress the first spring, and the lever is movable in a second, opposite direction to compress the second spring.

18. A surgical method, comprising:
positioning an end effector having opposed jaws on a distal end of an elongate shaft of a surgical device in a body cavity, the surgical device having a trigger and a housing; and
moving a biasing switch on a handle of the surgical device to one of a first position in which the biasing switch biases the opposed jaws to a first configuration, and a second position in which the biasing switch biases the opposed jaws to a second configuration;
wherein when the biasing switch is in the second position, moving the trigger away from the housing causes the opposed jaws to open.

19. The method of claim 18, further comprising actuating a trigger on the handle to move the end effector from the first configuration to the second configuration.

20. The method of claim 18, further comprising moving the biasing switch on the handle to the other one of the first and second positions.

21. The method of claim 18, wherein the opposed jaws are open in the first configuration and closed in the second configuration.

* * * * *